(12) United States Patent
Haseltine

(10) Patent No.: US 11,612,540 B2
(45) Date of Patent: *Mar. 28, 2023

(54) SELF-HEATING AND HARDENING VIBRATING SENSUAL STIMULATION DEVISE

(71) Applicant: Loanna Haseltine, Paris (FR)

(72) Inventor: Loanna Haseltine, Paris (FR)

(*) Notice: Subject to any disclaimer, the term of this patent is extended or adjusted under 35 U.S.C. 154(b) by 295 days.

This patent is subject to a terminal disclaimer.

(21) Appl. No.: 16/844,834

(22) Filed: Apr. 9, 2020

(65) Prior Publication Data

US 2020/0230019 A1 Jul. 23, 2020

Related U.S. Application Data

(62) Division of application No. 15/657,874, filed on Jul. 24, 2017, now Pat. No. 10,646,398.

(60) Provisional application No. 62/365,627, filed on Jul. 22, 2016.

(51) Int. Cl.
| | | |
|---|---|---|
| *A61H 19/00* | (2006.01) | |
| *A61H 23/02* | (2006.01) | |
| *A61F 7/12* | (2006.01) | |
| *A61N 7/00* | (2006.01) | |
| *A61F 7/00* | (2006.01) | |

(52) U.S. Cl.
CPC ............... *A61H 19/32* (2013.01); *A61F 7/12* (2013.01); *A61H 19/44* (2013.01); *A61H 23/02* (2013.01); *A61F 2007/005* (2013.01); *A61F 2007/0087* (2013.01); *A61F 2007/126* (2013.01); *A61H 2201/0207* (2013.01); *A61H 2201/10* (2013.01); *A61H 2201/1207* (2013.01); *A61N 7/00* (2013.01)

(58) Field of Classification Search
CPC ........ A61H 19/00; A61H 19/30; A61H 19/32; A61H 19/34; A61H 19/40; A61H 19/44; A61H 23/00; A61H 23/02
See application file for complete search history.

(56) References Cited

U.S. PATENT DOCUMENTS

| | | |
|---|---|---|
| 3,938,018 A | 2/1976 | Dahi |
| 4,077,390 A | 3/1978 | Stanley et al. |
| 5,952,814 A | 9/1999 | Van Lerberghe |

(Continued)

FOREIGN PATENT DOCUMENTS

| | | |
|---|---|---|
| DE | 299 21 064 U1 | 5/2000 |
| DE | 20 2006 010 236 U1 | 1/2007 |

(Continued)

*Primary Examiner* — John P Lacyk
(74) *Attorney, Agent, or Firm* — Nixon & Vanderhye

(57) ABSTRACT

A medical, or fertility aid, or sensual device including: an outer cylindrical phallic shaped outer cover; a cylindrical phallic shaped liquid filled enclosed casing pocket; rechargeable vibrating/infrared/ultrasound core inserted into the outer cover, wherein the liquid filled pocket contains a ferrous metal disk which can be bent; and a sheath encasing the outer cover. One embodiment relates to a vibrating, and or infrared, and/or ultrasound, and heat emitting and self-hardening dildo fertility devise which offers a solution for women with endometrial or uterine caused infertility. It can also be used as an aid in re-habilitation for women recovering from trauma to the vagina due to radiation therapy in the treatment of cervical and uterine cancers.

11 Claims, 3 Drawing Sheets

(56) References Cited

U.S. PATENT DOCUMENTS

| | | | | |
|---|---|---|---|---|
| 9,649,249 | B1* | 5/2017 | Green | A61F 2/50 |
| 10,646,398 | B2* | 5/2020 | Haseltine | A61H 19/44 |
| 2009/0171144 | A1* | 7/2009 | Squicciarini | A61H 19/32 |
| | | | | 600/38 |
| 2010/0268021 | A1* | 10/2010 | Standfest | A61H 15/0078 |
| | | | | 600/38 |
| 2012/0136205 | A1 | 5/2012 | Aguilera Galeote | |
| 2014/0148740 | A1* | 5/2014 | Howsam | A61H 23/0263 |
| | | | | 206/524.1 |
| 2014/0163437 | A1* | 6/2014 | Mack | A61H 19/40 |
| | | | | 601/46 |
| 2015/0174001 | A1* | 6/2015 | Milton | A61H 19/32 |
| | | | | 600/41 |
| 2017/0281459 | A1 | 10/2017 | Cirillo-Schmidt | |

FOREIGN PATENT DOCUMENTS

| | | |
|---|---|---|
| DE | 20 2009 000 723 U1 | 5/2009 |
| DE | 20 2009 000 725 U1 | 5/2009 |

* cited by examiner

SELF-HEATING AND HARDENING VIBRATING SENSUAL STIMULATION DEVISE

FIELD OF INVENTION

The present invention relates to a heating device comprising of a cylindrical phallic shaped outer cover; a cylindrical phallic shaped rechargeable vibrating, and/or infrared, and/or ultrasound producing core inside said outer cover, which is contained and/or removable from the outer liquid filled pocket, wherein said liquid filled pocket contains a ferrous metal disk which can be bent; and a pliable textured sheath encasing previous described liquid pocket.

PRIOR ART

Sensual stimulation devises have existed in one form or other for centuries. Their shape and appearance have evolved following the technological advancements available through time. The usual approach has been to create the most authentic sensation to a real penis or vagina. Latest models are powered with vibrators and battery operated. Heating models do exist on the market. No devise or fertility aid exists currently as a home-use hand-held using infrared or ultrasound emitter. Existing devises are usually battery powered and have exterior controls connected with electrical cables. These need an outside power source to be operated and cannot be used in situations where this is not available. Also these models are unreliable for if batteries run low one must stop to go out and purchase the needed batteries. These forms of the devises are awkward and not echo-friendly and are poor estimations of the real thing. Heating pads using sodium acetate trihydrate have existed since 1978: U.S. Pat. No. 4,077,390. Since then there is prior art existing which uses a sodium acetate trihydrate reaction in a sexual stimulation devise. DE29921064U1, DE202006010236U1, DE202009000725U1 and DE202009000723U1. These devises miss the mark by not using an advantageous component.

Without vibration the hardening effect becomes extremely solid like granite but by use of a vibrating core the salt crystals harden yet still stay slightly malleable like a sand filled cushion and much more similar to a real penis or organic substance.

Currently 25% of infertility in women is due at least partially to a problem with the endometrial uterine lining. There is very little treatment available for this type infertility besides surrogacy. All treatments either mechanical or medicinal involve increasing the blood-flow to the uterus and sexual organs. Very rarely do the current treatments work as heat is placed relatively far from the sexual organs. The invention by way of using a vibrating, and/or infrared, and/or ultrasound emitting core increases sensation and blood-flow to the sexual organs to increase fertility while the vibration itself has a dramatic effect on the liquid-solution chemical reaction. It can also be used as an aid in rehabilitation for women recovering from trauma to the vagina due to radiation therapy in the treatment of cervical and uterine cancers.

The vibrator, and/or infrared, and/or ultrasound component is rechargeable by use of an induction charging system. U.S. Pat. No. 3,938,018 (year 1974) and U.S. Pat. No. 5,952,814 (year 1987).

In contrast the entire exterior housing of the present invention is completely self-contained (closed) with no seams or opening. The vibrating and/or infrared, and/or ultrasound insert is completely self contained (closed) with no seams or opening or removable from this housing liquid pocket. The devise is re-usable by removing the textured outer sheath and vibrating, and/or infrared, and/or ultrasound emitting insert and submerging the liquid pocket housing part of the devise in a 95° Celsius water bath for 30-60 minutes and thereby returning the chemical liquid agent to it's liquid state by heating. This process melts the hardened sodium acetate trihydrate salt crystals which returns to a liquid state by endothermically storing the kinetic heat from the water bath.

SUMMARY OF THE INVENTION

The present invention relates to a medical, or fertility aid, or sensual device comprising a cylindrical phallic shaped and/or textured and/or pliable outer cover; a cylindrical phallic-shaped rechargeable vibrating and/or infrared, and/or ultrasound core inside said outer cover an enclosed liquid filled pocket or a removable cylindrical phallic-shaped rechargeable vibrating, and or infrared, and/or ultrasound core insert. Wherein said liquid filled pocket contains a ferrous metal disk which can be bent; and a pliable sheath encasing said outer cover in one embodiment.

The medical, or fertility aid, or sensual device, as described herein, wherein said liquid filled pocket containing a liquid which is a chemical salt solution of food-grade sodium acetate trihydrate.

The medical, or fertility aid, or sensual device, as described herein, also has a metal disk; when said metal disk is bent after which it snaps back into its original shape—a chemical reaction in said liquid pocket is created in which the liquid therein hardens and releases exothermic heat while converting from a liquid to a solid.

The vibration of the inner core keeps the chemical salt solution from completely hardening and increases the duration time of exothermic heat.

The sheath is 2 mm or wider in thickness and is removable, washable and replaceable—and is made of a textured pliable material.

The medical, or fertility aid, or sensual device, as described herein, can further have a base charging unit detached from said sensual device. This base charging unit can be connected to an electrical wall unit, cigarette lighter unit, a USB connection or by inserting into a solar-powered-pack unit.

In another embodiment a sensual device comprising of a cylindrical phallic-shaped hollow tube with one end closed and the other end open; a vibrating device placed at the bottom closed end of said cylindrical phallic shaped hollow tube, wherein said cylindrical phallic shaped hollow tube is lined with a cylindrical pocket tubular in shape with a hollow core wherein said cylindrical pocket contains a ferrous metal disk which can be bent; and a sheath encasing said outer cover is disclosed.

Like the first embodiment, the cylindrical pocket can contain a liquid which is a chemical salt solution of food-grade sodium acetate trihydrate; when said metal disk is bent after which it snaps back into its original shape—a chemical reaction in said liquid pocket is created in which the liquid therein hardens and releases exothermic heat while converting from a liquid to a solid; the vibration of the inner core keeps the chemical salt solution from completely hardening and increases the duration time of exothermic heat; and the sheath is 3 mm or wider in thickness and is removable, washable or replaceable and is made of a textured pliable material.

The medical, or fertility aid, or sensual device, as described herein, can further have a base charging unit detached from said sensual device. This base-charging unit can be connected to an electrical wall unit, cigarette lighter unit, a USB connection or by inserting into a solar-powered-pack unit.

DETAILED DESCRIPTION OF THE PREFERRED EMBODIMENTS

The invention is described here in two possible embodiments: 1. As a Dildo—a vaginal stimulator, or 2. a masturbator—for penile stimulation.

1. Dildo:

By use of a phallic shaped pocket with an inner core vibrating, and/or infrared, and/or ultrasound devise powered by a magnetic/induction charge. This inner core is surrounded by a food-grade sodium acetate trihydrate that hardens and heats when friction is applied by bending a ferrous metal disk—changing it from a liquid to a sold crystal state while giving off a radiating heat. After use the liquid pocket housing is removed and immersed in near boiling water to re-charge the hardened chemical crystals which is rechargeable endothermically with kinetic heat from the hot water bath and regains it's liquid state. The hardened crystals are stiff yet malleable and/or can be molded to take the shape desired by the user. Also the chemical components are echo-friendly, and it does not use batteries for the heating process; and a rechargeable one for the vibrator, and/or infrared, and/or ultrasound component—so the devise creates less waste for the environment. If the vibrator, and/or infrared, and/or ultrasound component is not used the apparatus will still be effective due to the hardening/heating effect so can it be used in places where electricity or AC/DC or not enough solar light is available.

2. Masturbator

The masturbator consists of 1. Cylindrical hard plastic tube with hollow center with one end closed and the other end open. At the base of the hard plastic shell lies the vibrating, and/or infrared, and or ultrasound devise powered by an induction magnetic charge. Filling the exterior plastic shell is the removable flexible inner-tube filled with a food-grade sodium acetate trihydrate (a non-Newtonian Fluid) which hardens and heats when the ferrous metal disk is bent- and changing it from a liquid to a solid crystal state while giving off a radiating heat.

An inner changeable sheath which lines the inside of the inner-tube completes the apparatus. This masturbator when changing from a liquid to a solid takes the form/size of the user while creating pressure and heat against the phallus of the user. It is echo-friendly, and it does not use consumable batteries. If the vibrator is not used the apparatus will still be effective due to the hardening/heating effect so can it be used in places where electricity or AC/DC or not enough solar light is available.

Figure 1:
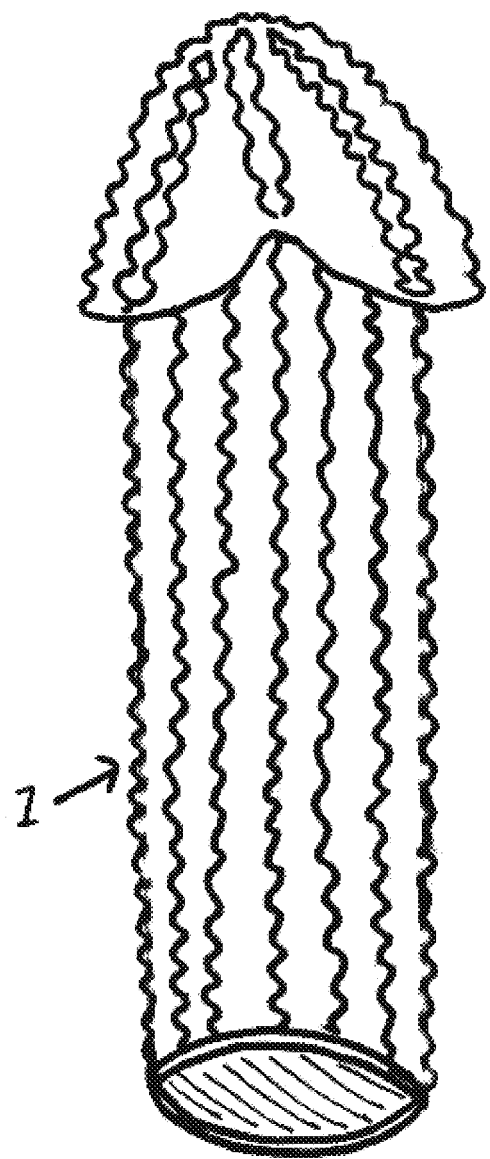
FIG. 1 is a drawing of the exterior inter-changeable textured sheath (1)
Figure 2:
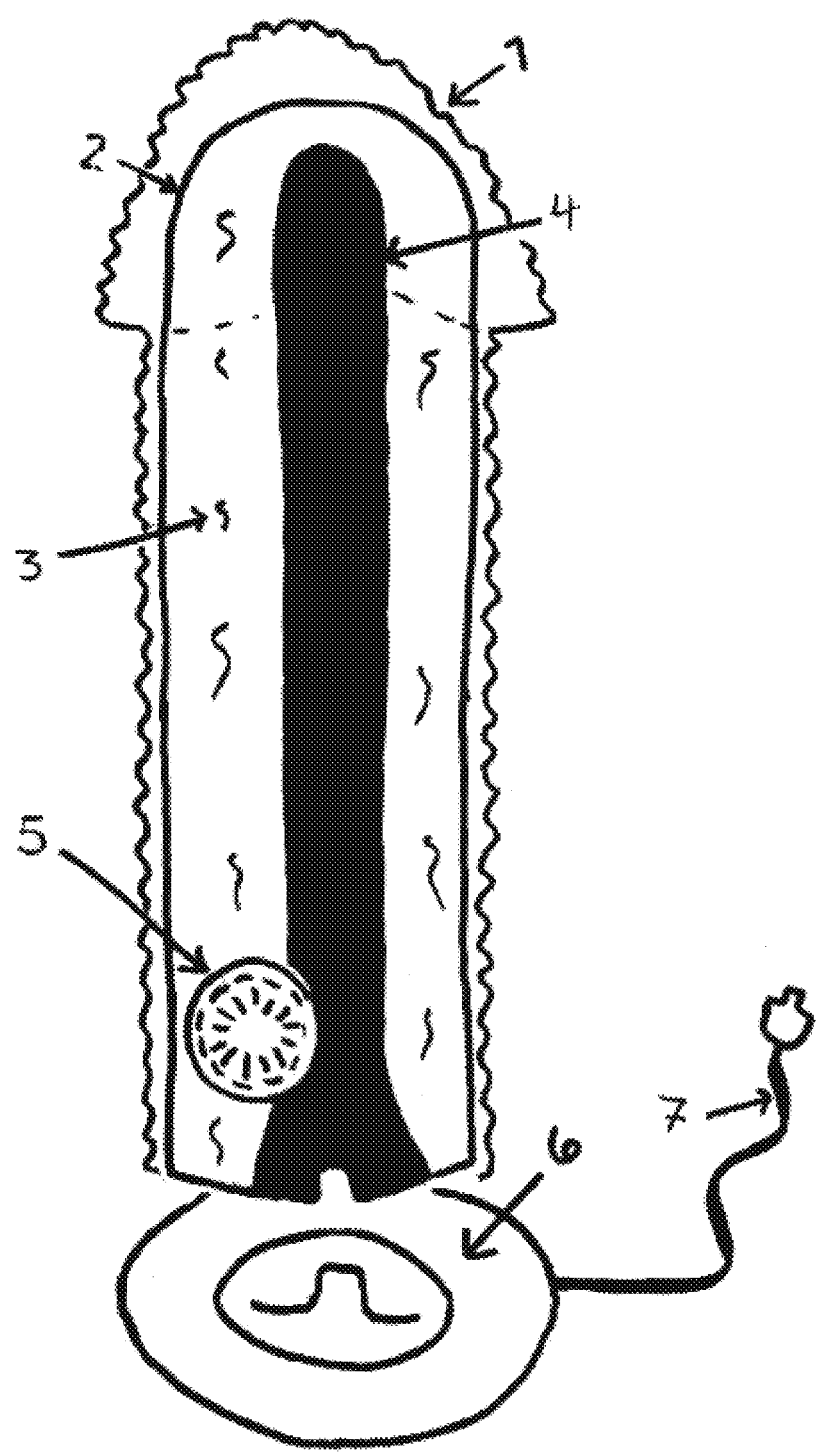
FIG. 2 is an Illustration of a dildo having:
an exterior inter-changeable textured sheath (1);
an inner-tube containing liquid heating/hardening salts (2);
liquid heating/hardening salts (3);
an inner-core vibrator, Or removable vibrator and/or infrared, and/or ultrasound insert (4);
a ferrous metal catalyst disk which starts chemical conversion (5);
a magnetic/induction charger for vibrator/infrared/ultrasound component (6);
a charging lead for USB or electrical outlet or solar-powered pack unit (7)

In one aspect of the present invention relates to a dildo, which is a stimulator, or medical or fertility aid devise, which increases blood flow to the sexual organs: FIG. 2

This embodiment relates to a method utilizing the apparatus as described herein in the aspect of a dildo. This method of using the apparatus is for medical usage in aid of fertility, or vaginal rehabilitation after radiation cancer treatment. By inserting the apparatus in the vagina it's heating and vibrating action will promote increased blood flow to the reproductive organs. Traditional methods have required using hot-water-bottles or heat packs to the surface of the pelvic region, over the uterus and ovaries. By using the apparatus through vaginal insertion the heating effect is located even closer to the reproductive organs and therefore has a more dramatic effect on increasing blood flow to those areas. In addition the vibrating, and/or infrared, and/or ultrasound attributes of the apparatus creates an increase in its effectiveness: which completely surpasses conventional methods.

In this embodiment the invention relates to a vibrating, and/or infrared, and/or ultrasound, and heat emitting and self hardening dildo medical or fertility devise which offers a solution for women with endometrial or uterine caused infertility. It can also be used as an aid in re-habilitation for women recovering from trauma to the vagina due to radiation therapy in the treatment of cervical and uterine cancers.

This is a Bullet or phallic-shaped fertility aid or stimulation devise consisting of the Sheath (1) which is a changeable and renewable component and an accessory to the devise. The sheath allows increased friction and the desired sensation to be customized. By changing the sheath materials, thickness and form it is also possible to regulates the amount of heat expelled from the devise.

This sheath can be manufactured in an array of materials that offer a diversity of textured sensations to be exploited by the user of the devise. Inside the sheath lies the inner tube housing (2) which exterior surface is made of a transparent flexible silicone;

flexible transparent elastomeric plastic or latex derivative or other transparent elastomeric watertight and heat resistant material—molded and seamless in its manufacture. This housing is self-contained without opening or seams which contains a liquid solution of food-grade sodium acetate trihydrate ($CH_3COONa3H_2O$) (3) floating in this fluid is a flat ferrous metal disk catalyst (5). The devise has a center core structure insert—which is a rechargeable vibrating, and/or infrared, and/or ultrasound emitting apparatus— which may, or may not be removable from the liquid pocket housing (4). This inner core apparatus is rechargeable by use of an induction charging system. U.S. Pat. No. 3,938,018 (year 1974) and U.S. Pat. No. 5,952,814 (year 1987) This phallic-shaped liquid filled vibrating, and/or infrared, and/or ultrasound emitting devise has a final component consisting of the charging hub (6) for the devise which makes use of induction/magnetic charge for the rechargeable battery (See prior art referenced in paragraph above) contained in the vibrating, and/or infrared, and/or ultrasound emitting inner core of the devise. In this way the unit can be completely immersed in water without disrupting the interior electrical mechanical vibrating core. This charger component makes use of a electrical wall outlet or USB connection or solar-powered pack (7) and transfers this energy into a magnetic field that charges the apparatus when placed it its charging hub. The liquid component filling the inner tube structure of the devise is a liquid solution of food-grade sodium acetate trihydrate—($CH_3COONa3H_2O$) is the heating and hardening element of the devise. Sodium acetate trihydrate, is a non-Newtonian fluid and it's natural resting state is a salt crystal. When bending the inner ferrous metal disk creates friction. As the disk rubs against the surrounding molecules—it behaves as a catalyst creating a chain reaction in the other surrounding molecules. Once one molecule is disrupted "bumped" it expands into its relaxed naturally solid form. This movement causes the molecule to bump against other surrounding molecules which in-turn affects those adjacent. The reaction of the expanding and changing structure of the molecule gives off a radiating heat which peaks after 15-20 minutes at approximately 55° Celsius which is 20° Celsius above body temperature. The derivative heat from the reaction cools slowly over the next hour and finally dispersing completely to room temperature. Room temperature being achieved two hours after initial cause reaction. By this process the liquid chemical core filling heats and hardens. Note: Sodium acetate trihydrate—($CH_3COONa3H_2O$)—a crystalline salt that is food-grade and currently used as an flavor additive in the USA food industry.

Figure 3:
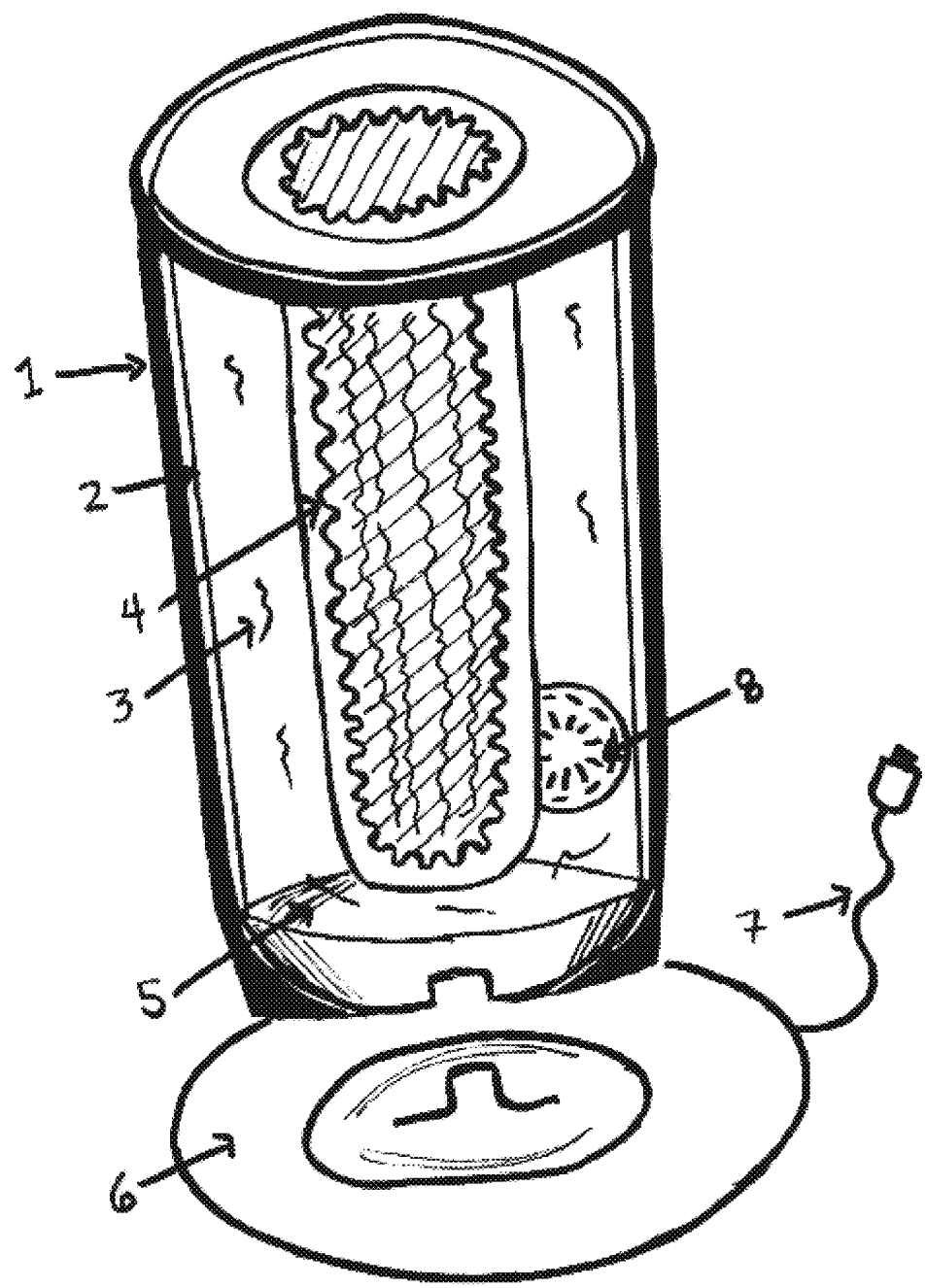
FIG. 3 is an illustration of a masturbator having:
a plastic shell (1);
An inner-tube containing liquid heating/hardening salts (2);
liquid heating/hardening salts (3);
an interior changeable sheath (4);
an inner core vibrator and/or infrared and/or ultrasound component (5);
a magnetic/induction charger for vibrator and/or infrared, and/or ultrasound component (6);
a charging lead for USB or electrical outlet solar-powered pack unit (7);
a ferrous metal catalyst disk which starts chemical conversion (8)

In another aspect of the present invention as a masturbator for penile stimulation: FIG. 3

The masturbator consists of cylindrical hard plastic housing with hollow center (1). Filling the exterior plastic shell is the removable flexible inner-tube (2) filled with a food-grade chemical solution (3) sodium acetate trihydrate ($CH_3COONa3H_2O$) which hardens and heats when friction is applied changing it from a liquid to a sold crystal state while giving off a radiating heat (a non-Newtonian Fluid). Floating in this fluid is the inner ferrous metal disk (8) when bent it disrupts the surrounding molecules. This catalyst creates a chain reaction in the molecules, which creates the crystallizing effect which subsequently gives off radiating heat. Lining this liquid filled inner-tube is the inner changeable sheath (4) At the base of the devise and attached to the bottom the hard plastic shell lies the vibrating, and/or infrared, and/or ultrasound emitting component (5) powered by an induction magnetic charging hub (6) and electrical or USB power cord (7) completing the apparatus. This masturbator when changing from a liquid to a solid takes the form/size of the user while creating pressure and heat against the phallus of the user.

What is claimed is:

1. A fertility device comprising:
   (i) an outer cylindrical cover;
   (ii) a cylindrical rechargeable infrared core insert inside said outer cover; and
   (iii) a sheath encasing said outer cover.

2. The fertility device according to claim 1, wherein the sheath is 3 mm in thickness and is removable, washable or replaceable.

3. The fertility device according to claim 1, wherein said sheath is made of a textured material.

4. The fertility device according to claim 1, further comprising a charging port in said cylindrical rechargeable infrared core insert and a base-charging unit detached from said charging port.

5. The fertility device according to claim 1, further comprising a connector for connecting said rechargeable infrared core insert to an electrical wall unit, cigarette lighter unit, a USB connection or by inserting into a solar-powered pack unit.

6. A fertility device comprising:
   (i) a cylindrical hollow tube with one end closed and the other end open;
   (ii) an infrared device placed at the closed end of said cylindrical hollow tube; and
   (iii) a sheath encasing said cylindrical hollow tube.

7. The fertility device according to claim 6, wherein the sheath is 3 mm in thickness and is removable, washable or replaceable.

8. The fertility device according to claim 6, wherein said sheath is made of a textured material.

9. The fertility device according to claim 6, further comprising a charging port in said infrared device and a base-charging unit detached from said charging port.

10. The fertility device according to claim 9, further comprising a connector for connecting said infrared device to an electrical wall unit, cigarette lighter unit, a USB connection or by inserting into a solar-pack unit.

11. The fertility device according to claim 6, wherein said cylindrical rechargeable infrared device is removable from said cylindrical hollow tube.

* * * * *